US00PP22563P2

(12) United States Plant Patent
Gomez Bullis

(10) Patent No.: US PP22,563 P2
(45) Date of Patent: Mar. 6, 2012

(54) ***NEOREGELIA* PLANT NAMED 'TATIANA'**

(50) Latin Name: ***Neoregelia* hybrid**
Varietal Denomination: Tatiana

(75) Inventor: Patricia E. Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 0 days.

(21) Appl. No.: 12/806,814

(22) Filed: Aug. 21, 2010

(51) Int. Cl.
*A01H 5/00* (2006.01)

(52) U.S. Cl. ..... Plt./370

(58) Field of Classification Search ..... Plt./370
See application file for complete search history.

*Primary Examiner* — June Hwu

(74) *Attorney, Agent, or Firm* — C. A. Whealy

(57) ABSTRACT

A new and distinct cultivar of *Neoregelia* plant named 'Tatiana', characterized by its upright and outwardly arching growth habit; broad glossy green and purple-colored lower leaves; broad glossy red purple-colored upper leaves; good interiorscape and landscape performance; and resistance to leaf spotting pathogens.

1 Drawing Sheet

Botanical designation: *Neoregelia* hybrid.
Cultivar denomination: 'TATIANA'.

BACKGROUND OF THE INVENTION

The present invention relates to a new and distinct cultivar of *Neoregelia* plant, botanically known as *Neoregelia* hybrid, and hereinafter referred to by the name 'Tatiana'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of *Neoregelia* hybrid 'Purple Star', not patented, as the female, or seed, parent with *Neoregelia* hybrid 'Autumn Leaves', not patented, as the male, or pollen, parent. The new *Neoregelia* plant was discovered and selected by the Inventor as a single plant within the progeny of the stated cross-pollination in a controlled greenhouse environment in Princeton, Fla. in 2002.

Asexual reproduction of the new *Neoregelia* plant by offsets in a controlled environment in Princeton, Fla. since 2003, has shown that the unique features of this new *Neoregelia* plant are stable and reproduced true to type in successive generations.

SUMMARY OF THE INVENTION

Plants of the new *Neoregelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Tatiana'. These characteristics in combination distinguish 'Tatiana' as a new and distinct cultivar of *Neoregelia:*

1. Upright and outwardly arching growth habit.
2. Broad glossy green and purple-colored lower leaves.
3. Broad glossy red purple-colored upper leaves.

4. Good interiorscape and landscape performance.
5. Resistant to leaf spotting pathogens.

Plants of the new *Neoregelia* differ primarily from plants of the female parent, 'Purple Star', in the following characteristics:

1. Plants of the new *Neoregelia* have broader leaves than plants of 'Purple Star'.
2. Leaves of plants of the new *Neoregelia* develop their purple to red purple coloration months earlier than plants of 'Purple Star'.
3. Plants of the new *Neoregelia* are more resistant to fungal pathogens especially under hot and wet conditions than plants of 'Purple Star'.

Plants of the new *Neoregelia* differ primarily from plants of the male parent, 'Autumn Leaves', in the following characteristics:

1. Plants of the new *Neoregelia* do not require flower bud initiation to develop leaf coloration whereas plants of 'Autumn Leaves' require flower bud initiation to develop leaf coloration.
2. Lower leaves of plants of the new *Neoregelia* are purple in color whereas lower leaves of plants of 'Autumn Leaves' are green to bronze in color.
3. Upper leaves of plants of the new *Neoregelia* are red purple in color whereas upper leaves of plants of 'Autumn Leaves' are pink in color.

Plants of the new *Neoregelia* can be compared to plants of the *Neoregelia* 'Royal Burgundy', not patented. In side-by-side comparisons conducted in Princeton, Fla., plants of the new *Neoregelia* and 'Royal Burgundy' differed primarily in the following characteristics:

1. Plants of the new *Neoregelia* had broader leaves than plants of 'Royal Burgundy'.
2. Plants of the new *Neoregelia* and 'Royal Burgundy' differed in leaf coloration.

Plants of the new *Neoregelia* can also be compared to plants of the *Neoregelia* 'Purple Rain', not patented. In side-by-side comparisons conducted in Princeton, Fla., plants of the new *Neoregelia* and 'Purple Rain' differed primarily in the following characteristics:

1. Plants of the new *Neoregelia* had broader leaves than plants of 'Purple Rain'.
2. Plants of the new *Neoregelia* did not require flower bud initiation to develop leaf coloration whereas plants of 'Purple Rain' required flower bud initiation to develop leaf coloration.
3. Plants of the new *Neoregelia* and 'Purple Rain' differed in leaf coloration.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph at the bottom of the sheet is a side perspective view of a typical flowering plant of 'Tatiana' grown in a container.

The photograph at the top of the sheet is a top perspective view of a typical flowering plant of 'Tatiana'.

DETAILED BOTANICAL DESCRIPTION

The aforementioned photographs and following observations, measurements and values describe flowering plants grown during the spring in 15-cm containers in a polypropylene-covered greenhouse in Princeton, Fla. under commercial *Neoregelia* production practices. During the production of the plants, day temperatures ranged from 10° C. to 32° C., night temperatures ranged from 7° C. to 32° C. and light levels averaged 3,200 foot-candles. Plants were one year old when the photographs and description were taken. In the following description, color references are made to The Royal Horticultural Society Colour Chart, 2007 Edition, except where general terms of ordinary dictionary significance are used.

Botanical classification: *Neoregelia* hybrid 'Tatiana'.

Parentage:

*Female, or seed, parent.*—*Neoregelia* hybrid 'Purple Star', not patented.

*Male, or pollen, parent.*—*Neoregelia* hybrid 'Autumn Leaves', not patented.

Propagation:

*Type.*—By offsets.

*Time to initiate roots, summer.*—About 30 days at 28° C. to 30° C.

*Time to initiate roots, winter.*—About 50 to 60 days at 28° C. to 30° C.

*Time to produce a rooted young plant, summer.*—About three months at 28° C. to 30° C.

*Time to produce a rooted young plant, winter.*—About four months at 18° C. to 22° C.

*Root description.*—Medium in thickness, fibrous; brown to tan in color, apices yellow in color.

*Rooting habit.*—Moderately freely branching; medium density.

Plant description:

*Plant form/growth habit.*—Upright and outwardly arching growth habit; rosette leaves are erect when young, becoming outwardly arching with development; plants readily produce uniform offsets; vigorous growth habit.

*Plant height.*—About 20 cm.

*Plant diameter or spread.*—About 43 cm.

*Internode length.*—About 4 mm.

*Stem texture.*—Smooth, glabrous.

*Stem color.*—Close to NN155B.

Foliage description:

*Arrangement.*—Rosette, spiral phyllotaxis; simple; sessile, clasping.

*Shape.*—Oblong.

*Apex.*—Cuspidate.

*Base.*—Truncate.

*Margin.*—Serrate; spinose.

*Length.*—About 26 cm.

*Width, mid-section.*—About 7.8 cm.

*Width, base.*—About 10 cm.

*Texture.*—Smooth, glabrous; leathery; longitudinally ribbed.

*Luster.*—Glossy.

*Venation pattern.*—Parallel.

*Color.*—Lower leaves, upper surface: Close to 146A irregularly overlain with stripes and splotches close to 187A; towards the base, close to 186A to 186B; venation, close to 146A. Lower leaves, lower surface: Close to N186C; towards the apex, close to 187A; venation, close to 148A. Upper leaves, upper surface: Close to 71A; towards the apex, close to 187A; venation, close to 71A. Upper leaves, lower surface: Close to 72A; venation, close to 72A.

Inflorescence description:

*Inflorescence form.*—Terminal flat-topped compact corymb located inside the leaf rosette; about 92 flowers develop per inflorescence.

*Time to flower.*—Plants begin flowering about ten to twelve weeks after planting; plants flower naturally during the spring in Florida.

*Flower longevity.*—Individual flowers last about two to three days on the plant; flowers persistent.

*Fragrance.*—None detected.

*Inflorescence length.*—About 6.4 cm.

*Inflorescence diameter.*—About 5 cm.

*Flower size.*—Length: About 5.1 cm. Diameter: About 9 mm.

*Flower buds.*—Length: About 4.5 cm. Diameter: About 7 mm. Shape: Narrowly elongate. Color: Close to 91B.

*Petals.*—Quantity per flower: Three in a single whorl. Shape: Oblanceolate. Apex: Acuminate. Base: Truncate. Margin: Entire. Length: About 3.5 cm. Width: About 8 mm. Texture: Smooth, glabrous. Color: When opening, upper surface: Close to 94B. When opening, lower surface: Close to 94D. Fully opened, upper surface: Close to NN155D; towards the apex, close to 94A. Fully opened, lower surface: Close to NN155D; towards the apex, close to 94D.

*Flower bracts.*—Quantity per flower: One. Shape: Oblanceolate. Length: About 3.4 cm. Width: About 8 mm. Texture: Membraneous. Color: Close to 145A and 157D.

*Sepals.*—Quantity per flower: Three in a single whorl. Shape: Oblanceolate. Apex: Acuminate. Base: Truncate. Margin: Entire. Length: About 2.4 cm. Width: About 1 cm. Texture: Smooth, glabrous. Color, upper surface: Close to 145C. Color, lower surface: Close to 145A to 145B.

*Peduncles.*—Length: About 1 cm. Diameter: About 1.7 cm. Strength: Strong. Aspect: Typically erect. Texture: Smooth, glabrous. Color: Close to NN155C.

*Pedicels.*—Length: About 7 mm. Diameter: About 4 mm. Strength: Strong. Aspect: Typically erect to somewhat outward and curving upright. Texture: Smooth, glabrous. Color: Close to 155D.

*Stamens.*—Quantity per flower: Six. Filament length: About 1.6 cm; partially adnate to the petals. Filament color: Close to NN155D. Anther shape: Lanceolate. Anther length: About 6 mm Anther color: Close to 155A. Pollen amount: Moderate. Pollen color: Close to 158B.

*Pistils.*—Quantity per flower: One. Pistil length: About 3.7 cm. Stigma shape: Oval, elongated. Stigma color: Close to NN155C. Style length: About 2.2 cm. Style color: Close to NN155D. Ovary color: Close to NN155B.

*Fruit/seed.*—Fruit and seed production have not been observed on plants of the new *Neoregelia.*

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions and to have good garden performance.

Disease/pest resistance: Plants of the new *Neoregelia* have been observed to be resistant to leaf spotting during periods of hot and rainy weather. Resistance to pests and other pathogens common to *Neoregelia* plants has not been observed.

It is claimed:

1. A new and distinct *Neoregelia* plant named 'Tatiana' as illustrated and described.

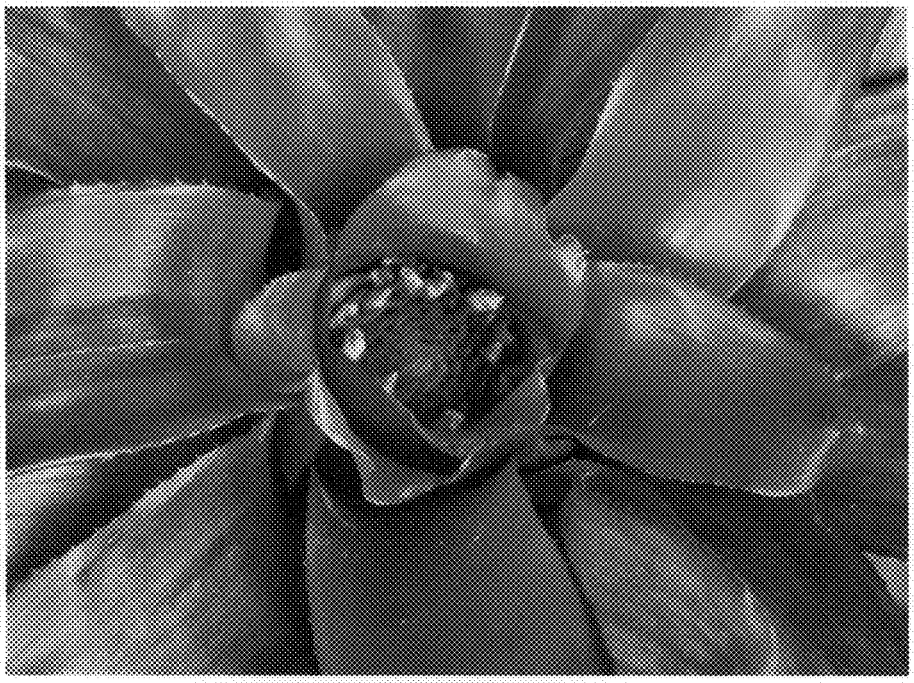
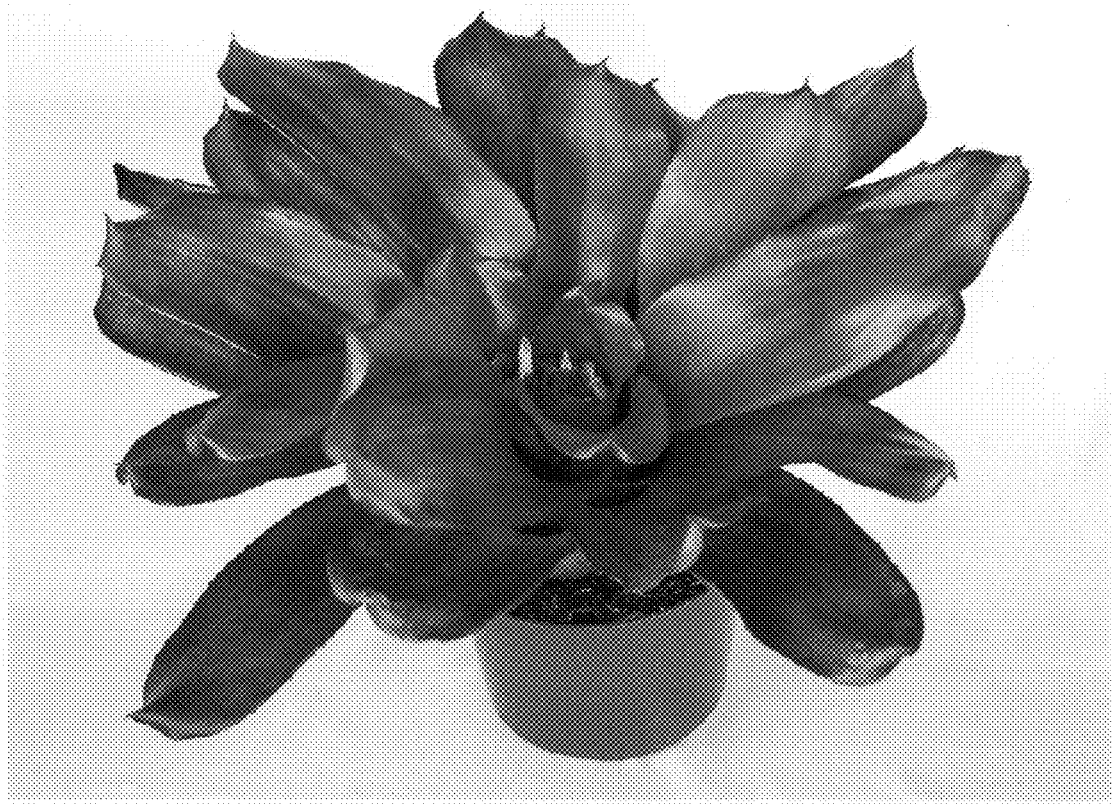

* * * * *